United States Patent
Otawara (10) Patent No.: US 7,914,440 B2
(45) Date of Patent: Mar. 29, 2011

(54) ENDOSCOPE

(75) Inventor: Takashi Otawara, Tokyo (JP)

(73) Assignee: Olympus Corporation (JP)

(*) Notice: Subject to any disclaimer, the term of this patent is extended or adjusted under 35 U.S.C. 154(b) by 858 days.

(21) Appl. No.: 11/618,419

(22) Filed: Dec. 29, 2006

(65) Prior Publication Data

US 2007/0232857 A1 Oct. 4, 2007

Related U.S. Application Data

(63) Continuation of application No. PCT/JP2005/012341, filed on Jul. 4, 2005.

(30) Foreign Application Priority Data

Jul. 2, 2004 (JP) .................................. 2004-197309

(51) Int. Cl.
*A61B 1/00* (2006.01)
(52) U.S. Cl. ........................................ 600/107; 600/104
(58) Field of Classification Search .................. 600/104, 600/106, 107, 127, 129, 146
See application file for complete search history.

(56) References Cited

U.S. PATENT DOCUMENTS

| | | | | |
|---|---|---|---|---|
| 4,589,403 A | * | 5/1986 | Ouchi et al. | 600/107 |
| 5,569,157 A | * | 10/1996 | Nakazawa et al. | 600/107 |
| 5,810,715 A | * | 9/1998 | Moriyama | 600/146 |
| 6,033,378 A | * | 3/2000 | Lundquist et al. | 604/95.01 |
| 2001/0037051 A1 | | 11/2001 | Fujii et al. | 600/146 |
| 2001/0044570 A1 | * | 11/2001 | Ouchi et al. | 600/107 |
| 2002/0091303 A1 | | 7/2002 | Otawara et al. | 600/106 |
| 2002/0161355 A1 | | 10/2002 | Wollschlager | 606/1 |
| 2003/0040657 A1 | * | 2/2003 | Yamaya et al. | 600/107 |
| 2004/0049095 A1 | * | 3/2004 | Goto et al. | 600/107 |
| 2004/0050416 A1 | * | 3/2004 | Kunkler | 137/112 |
| 2005/0096590 A1 | * | 5/2005 | Gullickson et al. | 604/95.04 |

FOREIGN PATENT DOCUMENTS

EP 1 302 151 A2 4/2003

OTHER PUBLICATIONS

International Search Report dated Aug. 23, 2005.
European Search Report dated Jul. 29, 2009.

* cited by examiner

*Primary Examiner* — John P Leubecker
*Assistant Examiner* — Victoria W Chen
(74) *Attorney, Agent, or Firm* — Ostrolenk Faber LLP (57) ABSTRACT

An endoscope according includes a treatment instrument riser which guides a distal end of a treatment instrument projected from a distal end opening provided in a channel for inserting the treatment instrument in an insertion portion to a desired position; a driving mechanism which is rotatably fitted onto an axis provided in an operation portion covered with an outer packaging member, and drives the treatment instrument riser; a guide-wire securing unit which secures a position of a guide wire projected from the distal end opening provided in the channel in the insertion portion; a guide-wire securing operation member which operates the guide-wire securing unit; and a securing unit which secures a position of the guide-wire securing operation member in a state where the position of the guide-wire is secured.

1 Claim, 11 Drawing Sheets

ENDOSCOPE

CROSS-REFERENCE TO RELATED APPLICATIONS

This application is a continuation of PCT international application Ser. No. PCT/JP2005/012341 filed Jul. 4, 2005 which designates the United States, incorporated herein by reference, and which claims the benefit of priority from Japanese Patent Application No. 2004-197309, filed Jul. 2, 2004, incorporated herein by reference.

BACKGROUND OF THE INVENTION

1. Field of the Invention

The present invention relates to an endoscope which is employed for treatment of an affected area and in which a guide wire is made to project from a distal-end opening provided in a treatment instrument insertion channel of an insertion portion and used as a guide to guide a treatment instrument to the affected area.

2. Description of the Related Art

According to conventionally known techniques, an operator carries out various treatments in body cavities by inserting an endoscope into the body cavities, selectively inserting various treatment instruments into a treatment instrument insertion channel arranged in an insertion portion of the endoscope, and projecting the treatment instrument from an opening provided at a distal-end portion of the endoscope.

The endoscope employed for the above treatments has a member (hereinafter referred to as distal-end hard portion), in which elements such as an objective lens are arranged, at a distal end of the insertion portion. In the distal-end hard portion, a tube-like member is arranged. The tube-like member penetrates the distal-end hard portion so as to guide the treatment instrument inserted into the treatment instrument insertion channel therein. A distal-end opening of the tube-like member is communicated with the opening of the distal-end portion of the endoscope. Further, an outer circumference of a proximal end of the tube-like member fits to an inner circumference of the distal end of the treatment instrument insertion channel, and is secured thereby. A proximal end of the treatment instrument insertion channel opens in an operation portion of the endoscope.

In recent years, so called side-looking type endoscopes provided with an imaging optical system on a side surface of a distal end of the insertion portion are employed for treatments of affected areas in alimentary tract system, pancreaticobiliary duct system, and the like. The side-looking type endoscope is employed for treatments of pancreaticobiliary duct system or the like, for example, for a preparatory treatment, in which contrast study is performed on a bile duct or a pancreatic duct with the endoscope, and for a therapeutic treatment, in which a gallstone present in a common bile duct or the like is removed with a use of a balloon, a grasper, or the like.

Since the pancreatic duct, bile duct, hepatic duct, and the like are extremely thin ducts, the insertion of the distal-end portion of the insertion portion of the endoscope into these ducts at the endoscopic treatment of the pancreatic duct, bile duct, hepatic duct, and the like is difficult to perform. Hence, the operator generally achieves the insertion of the insertion portion by: inserting the distal-end portion of the insertion portion of the side-looking type endoscope up to an area near a duodenal papilla, inserting a guide wire into a relevant duct from the side surface of the distal end of the insertion portion, in other words, through the opening provided at the distal end of the treatment instrument insertion channel in the insertion portion, under radioscopy, and selectively inserting a treatment instrument such as a catheter into the pancreatic duct, bile duct, or hepatic duct using the guide wire as a guide.

When the guide wire or the treatment instrument is to be inserted into the relevant duct from the opening in the distal end of the treatment instrument insertion channel in the insertion portion, a so-called treatment instrument riser is raised. The treatment instrument riser is arranged near the opening in the insertion portion and serves to change a direction of advance of the guide wire or the treatment instrument from a direction within the insertion portion of the endoscope to a direction toward the opening formed on the side surface.

According to the above technique, once the guide wire is inserted into a thin duct such as the pancreatic duct, bile duct, or hepatic duct, the treatment instrument can be inserted into and withdrawn from the above mentioned duct repeatedly.

When the treatment instrument is withdrawn from the pancreatic duct, bile duct, or hepatic duct, the guide wire is sometimes withdrawn together with the treatment instrument against the will of the operator due to close contact between the treatment instrument and the guide wire. Since the pancreatic duct, bile duct, or hepatic duct is an extremely thin duct, as described above, the insertion of the guide wire thereinto is difficult to perform. Therefore, it is extremely cumbersome and troublesome for the operator to reinsert the guide wire into the pancreatic duct, bile duct, hepatic duct or the like many times.

Hence, when the operator withdraws the treatment instrument, an assistant of the operator must keep inserting the guide wire toward the pancreatic duct, bile duct, or hepatic duct in order to prevent the withdrawal of the guide wire from the duct. Such an operation is extremely cumbersome for the operator and the assistant. As a result, the endoscopic diagnosis and treatment require high personnel cost, thereby placing a high financial burden on both the hospital and the patient.

In view of the foregoing, Japanese Patent Application Laid-Open No. 2002-34905, for example, proposes a technique for securing the guide wire at a certain position by: withdrawing the treatment instrument from the duct farther than a position where the guide wire is folded by the treatment instrument riser; rotating a treatment instrument riser operation knob provided rotatably in the operation portion; further raising the treatment instrument riser and thereby the guide wire; and sandwiching the guide wire between the treatment instrument riser and the distal end of the insertion portion of the endoscope.

The above-proposed structure is advantageous in that the guide wire would not be withdrawn from the duct when the treatment instrument is withdrawn, since the guide wire is secured between the treatment instrument riser and the distal end of the insertion portion of the endoscope.

SUMMARY OF THE INVENTION

An endoscope according to one aspect of the present invention includes a treatment instrument riser which guides a distal end of a treatment instrument projected from a distal end opening provided in a channel for inserting the treatment instrument in an insertion portion to a desired position; a driving mechanism which is rotatably fitted onto an axis provided in an operation portion covered with an outer packaging member, and drives the treatment instrument riser; a guide-wire securing unit which secures a position of a guide wire projected from the distal end opening provided in the channel in the insertion portion; a guide-wire securing operation member which operates the guide-wire securing unit; and a securing unit which secures a position of the guide-wire securing operation member in a state where the position of the guide-wire is secured.

An endoscope according to another aspect of the present invention includes a tube-like member for inserting a treatment instrument which is arranged so as to penetrate a hard portion arranged at a distal end of an insertion portion, one end of the tube-like member communicating with an opening formed at the distal end of the insertion portion; and a channel for inserting the treatment instrument which is arranged at the insertion portion, an opening of one end of the channel being fitted and secured at an outer circumference of another end of the tube-like member, and another end of the channel being opened to an operation portion. An inner diameter of the opening of the tube-like member is smaller than an inner diameter of the opening at the one end of the channel.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of an endoscope according to the present invention will be described below with reference to the accompanying drawings. It should be noted that the present invention is not limited to the embodiments.

Figure 1:
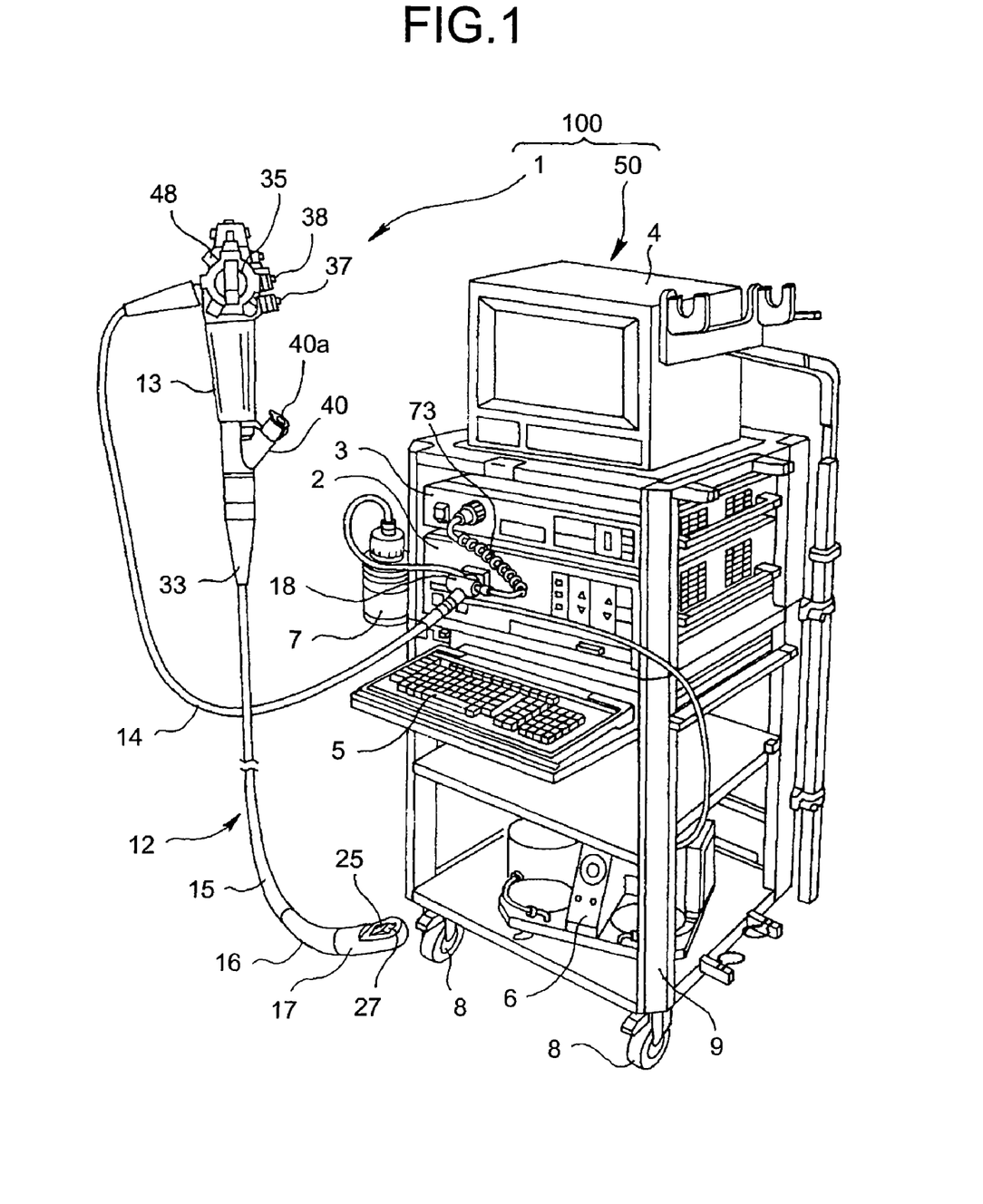
FIG. 1 is a perspective view of an endoscopic apparatus including an endoscope according to an embodiment of the present invention and a peripheral device thereof seen from above from a right-hand side.
Figure 2:
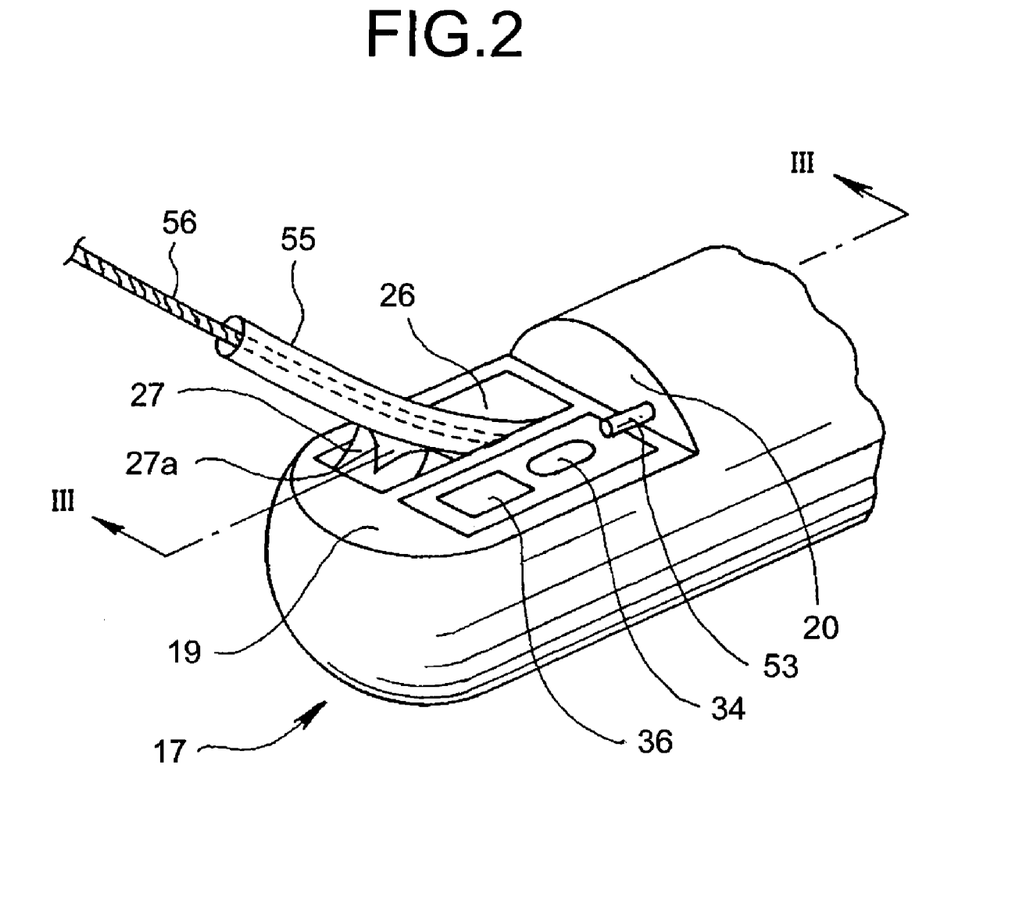
FIG. 2 is a partially enlarged perspective view of a distal-end portion of the endoscope of FIG. 1.

FIG. 1 is a perspective view of an endoscopic apparatus including an endoscope according to a first embodiment of the present invention and a peripheral device thereof seen from above from the right-hand side, and FIG. 2 is a partially enlarged perspective view of a distal-end portion of the endoscope of FIG. 1.

As shown in FIG. 1, an endoscopic apparatus 100 includes an endoscope 1 and a peripheral device 50. The endoscope 1 mainly includes an operation portion 13, an insertion portion 12, and a universal chord 14. An insertion portion protecting member 33 is arranged to protect the insertion portion 12 at a position where the insertion portion 12 and the operation portion 13 are connected.

The peripheral device 50 mainly includes various devices arranged on a counter 9 to which casters 8 are attached at a bottom portion. The peripheral device 50 includes, for example, a light source 2, a video processor 3, a connecting cable 73 which electrically connects the light source 2 and the video processor 3, a monitor 4, a keyboard 5, a suction pump device 6, and a water delivery bottle 7. Further, the endoscope 1 and the peripheral device 50 are connected to each other by a connector 18.

The connector 18 is connected to the light source 2 of the peripheral device 50. The connector 18 has a ferrule (not shown) which forms an end of a fluid pipe, a light guide ferrule (not shown) which forms an end of a light guide, and an electrical contact (not shown).

The light guide extends from the universal chord 14, penetrates through the operation portion 13 and the insertion portion 12, and reaches the distal-end portion 17 described later of the insertion portion 12, thereby transmitting illumination light emitted from the light source 2 toward an illumination lens 36 (see FIG. 2) of the distal-end portion 17 described later and further toward an interior of a body cavity in a radially expanded manner.

In the operation portion 13 of the endoscope 1, a bending operation knob 35, an air/water delivery operation button 37, a suction operation button 38, a treatment instrument riser operation knob (hereinafter simply referred to as operation knob) 48 which is employed for a raising operation of a treatment instrument riser 27 described later (see FIG. 2), and a treatment instrument insertion mouth 40 which has an opening 40a through which a treatment instrument is inserted into a treatment instrument insertion channel 23 (see FIG. 3) arranged inside the insertion portion 12 of the endoscope 1 are provided.

The insertion portion 12 of the endoscope 1 includes a distal-end portion 17, a bendable portion 16, and a flexible tube portion 15. The bendable portion 16 is manipulated so as to bend via the bending operation knob 35 provided in the operation portion 13, and is arranged between the distal-end portion 17 and the flexible tube portion 15.

As shown in FIG. 2, a portion of an outer circumference of the distal-end portion 17 is removed to form a cut-out portion 19 having a depressed shape, and a channel opening 26 which is located at a distal end side of the treatment instrument insertion channel 23 (see FIG. 3) is provided on an outer surface of the cut-out portion 19.

Further, an objective lens 34 of an imaging unit (not shown) housed in the distal-end portion 17 and an illumination lens 36 of an illumination optical system are arranged near the channel opening 26 on the outer circumference of the cut-out portion 19.

Further, a nozzle 53 for air and water delivery is projected from a wall surface 20 at a proximal end side of the cut-out portion 19 in the distal-end portion 17. When the air/water delivery operation button 37 in the insertion portion is operated and a fluid such as water and air is sprayed toward an outer surface of the objective lens 34 for cleaning of the objective lens 34, the fluid is ejected from the nozzle 53.

The treatment instrument riser 27 is arranged near the channel opening 26 in the distal-end portion 17. The treatment instrument riser 27 serves to raise a treatment instrument 55 or a guide wire 56. The treatment instrument riser 27 changes the direction of advance of the treatment instrument 55 inserted into the treatment instrument insertion channel from the opening 40a of the treatment instrument insertion mouth 40 or the guide wire 56 from the direction of advance in the treatment instrument insertion channel to the direction toward the channel opening 26 according to the rotation operation of the operation knob 48 via a riser driving mechanism 41 (see FIG. 7) and a raising wire 30 (see FIG. 3). The treatment instrument riser 27 secures the guide wire 56 at the position when raised to a maximum extent, and is a part of a guide-wire securing unit of the embodiment.

The guide wire 56 consists of a core wire of a superelastic alloy, for example, and a soft cladding of Teflon® or urethane, for example, which covers the core wire. When the treatment instrument such as a forceps and a catheter is to be selectively inserted into an extremely thin duct, such as the pancreatic duct, bile duct, hepatic duct, or the like with the use of the endoscope 1, the guide wire 56 is inserted into the duct before the insertion of the treatment instrument and thereby serving as a guide for the insertion of the treatment instrument into the duct.

Figure 3:
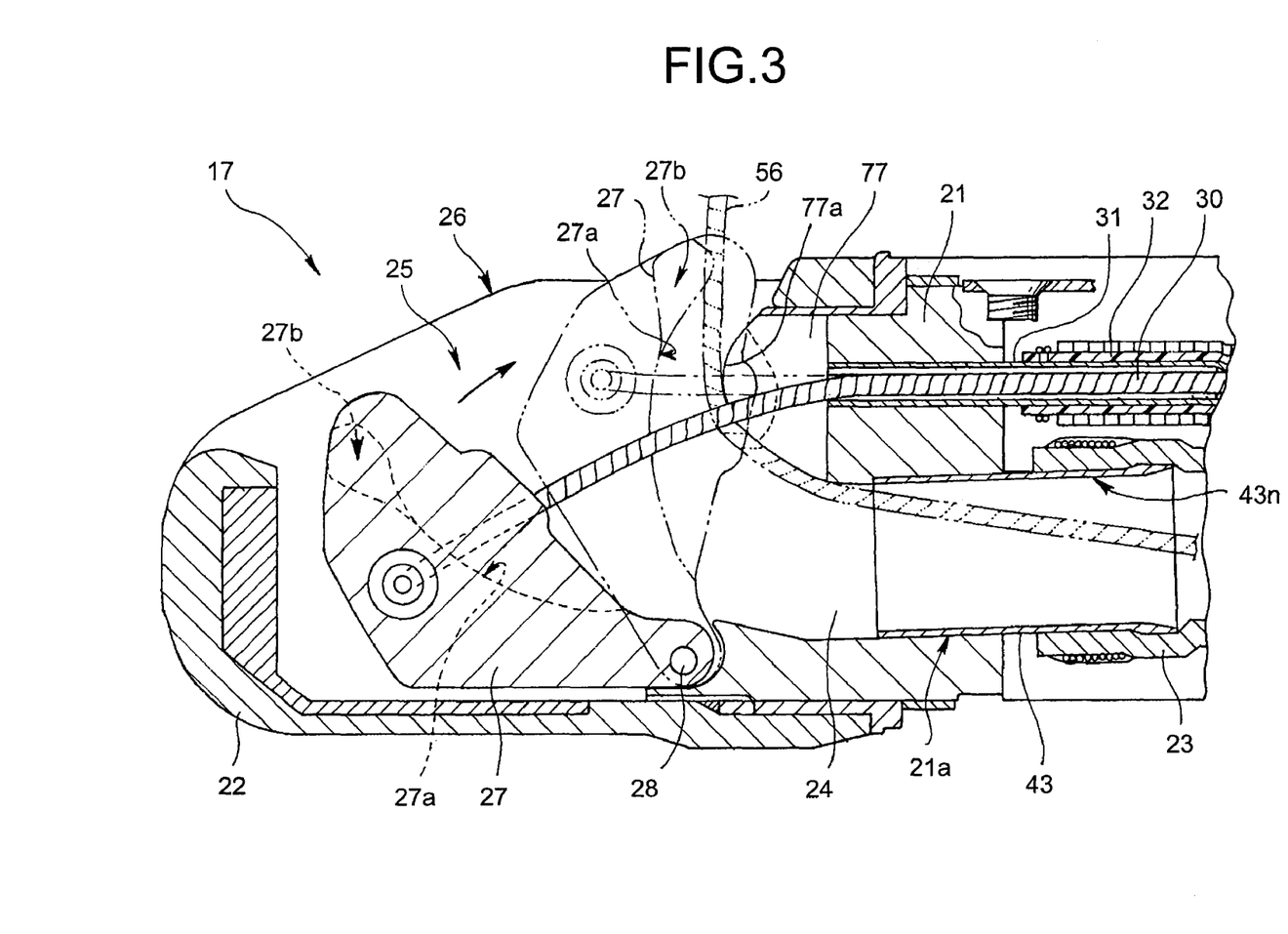
FIG. 3 is a sectional view along line III-III of FIG. 2.

In the following, an inner structure of the distal-end portion 17 of the endoscope 1, in particular, the treatment instrument riser 27, will be described schematically. FIG. 3 is a sectional view along line III-III of FIG. 2, FIG. 4 is an enlarged sectional view of a modified example of fitting between the connecting pipe arranged in the distal-end hard portion of FIG. 3 and the treatment instrument insertion channel, and FIG. 5 is a sectional view of an inner diameter portion of the connecting pipe of FIG. 4.

As shown in FIG. 3, the distal-end portion 17 includes the distal-end hard portion 21, which serves as a main body of the distal-end portion, and a distal-end cover 22 which is made of a non-conductive material such as resin and arranged so as to cover the distal-end hard portion 21. The distal-end cover 22 is fixed at a distal end of the distal-end hard portion 21 by a bonding agent or the like.

In the distal-end hard portion 21, an elongated hole 21a is formed along the insertion direction. A connecting pipe 43 which serves as a guiding path for the insertion of the treatment instrument 55 fits in the elongated hole 21a. A distal-end portion of the treatment instrument insertion channel 23, which serves as a guiding path for the treatment instrument 55, is fixed around an outer circumference of the connecting pipe 43 at a proximal end of the connecting pipe 43.

Figure 4:
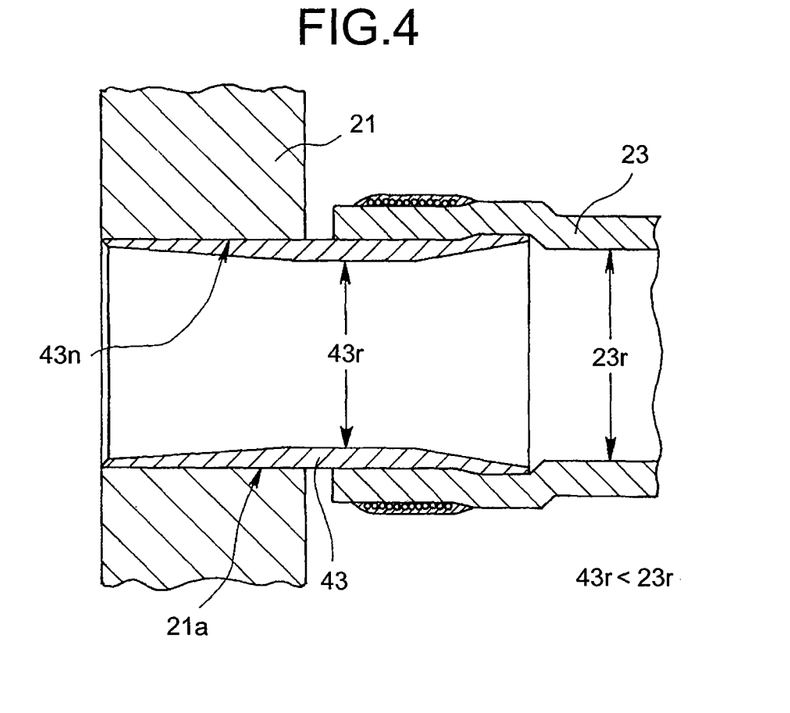
FIG. 4 is an enlarged sectional view of a modified example of fitting between a connecting pipe arranged in a distal-end hard portion and a treatment instrument insertion channel of FIG. 3.
Figure 5:
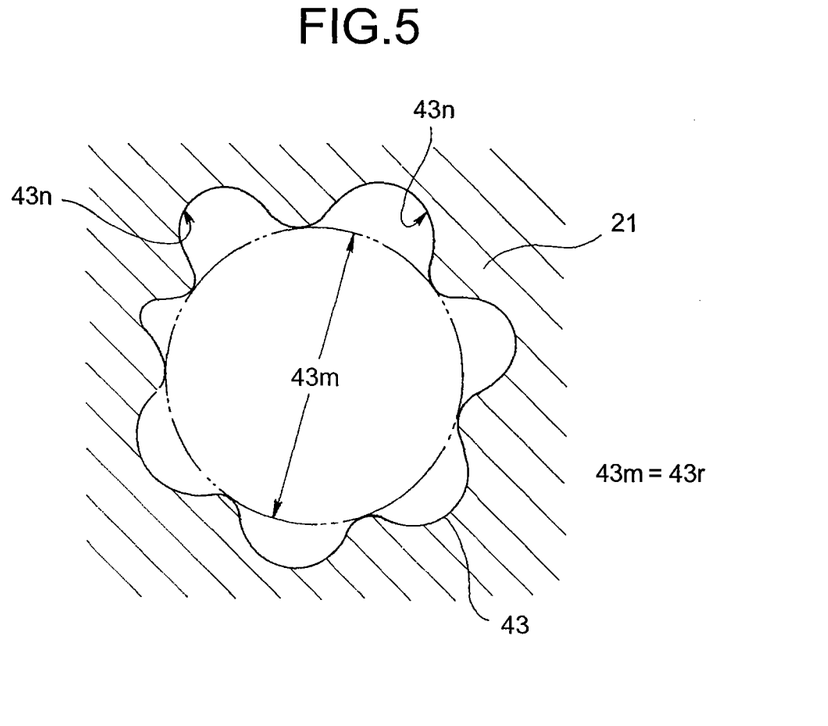
FIG. 5 is a sectional view of an inner diameter portion of the connecting pipe of FIG. 4.

As shown in FIG. 4, an inner diameter 43r of the connecting pipe 43 is preferably formed to be smaller than an inner diameter 23r of the treatment instrument insertion channel 23, and slightly larger than an outer diameter of the treatment instrument 55.

When the inner diameter 43r of the connecting pipe 43 is made slightly larger than the outer diameter of the treatment instrument 55, the treatment instrument 55 is prevented from being displaced when the treatment instrument 55 inserted into the treatment instrument insertion channel 23 from the opening 40a of the treatment instrument insertion mouth 40 of the endoscope 1 is made to be projected from the channel opening 26 of the distal-end portion 17.

Further, since the inner diameter 43r of the connecting pipe 43 is made smaller than the inner diameter 23r of the treatment instrument insertion channel 23 (i.e., the inner diameter 23r is made larger than the inner diameter 43r), the treatment instrument 55 can pass through the treatment instrument insertion channel 23 smoothly while the displacement of the treatment instrument 55 can be prevented by the connecting pipe 43. Therefore, the force required for the insertion of the treatment instrument at the insertion of the treatment instrument 55 into the treatment instrument insertion channel 23 and the connecting pipe 43 is reduced, and the insertability can be improved.

Further, as shown in FIG. 5, when a minimum diameter 43m of the inner diameter of the connecting pipe 43 satisfies the above condition for the inner diameter 43r, plural depressions may be formed on an inner diameter portion 43n of the connecting pipe 43. Not being limited by the above, the inner diameter portion 43n of the connecting pipe 43 may be formed in any shapes as far as the above condition is satisfied.

When the inner diameter portion 43n is formed in the modified shape as described above, the plural depressions serve to secure a sufficient amount of suction when the treatment instrument for suction or the like is inserted into the treatment instrument insertion channel 23 and the connecting pipe 43.

Returning to FIG. 3, a guiding path 24 is formed at the distal end side of the connecting pipe 43. The guiding path 24 communicates with the connecting pipe 43, and guides the treatment instrument 55 or the guide wire 56 toward the channel opening 26 side.

A housing chamber 25 is formed as a space surrounded by the distal-end hard portion 21 and the distal-end cover 22 at a distal end side of the guiding path 24. The housing chamber 25 has an opening which serves as the channel opening 26 that is the distal end opening of the treatment instrument insertion channel 23.

In the housing chamber 25, the treatment instrument riser 27 is arranged. The treatment instrument riser 27 is substantially triangular in section, and one end thereof is supported at a riser rotation support point 28 which serves as an axis and which is located at a lower part of the distal end opening of the guiding path 24 arranged in the distal-end hard portion 21. A portion around another end of the treatment instrument riser 27 rotates around the riser rotation support point 28 in the housing chamber 25.

The treatment instrument riser 27 has a guiding surface 27a in a position opposite to the channel opening 26. The guiding surface 27a is a groove with a substantially V-shaped section communicating with the guiding path 24 and serves to guide the treatment instrument 55 toward the channel opening 26. On a distal end side of the guiding surface 27a, a slit 27b is formed on a surface facing with the channel opening 26. When the treatment instrument riser 27 is raised, the guide wire 56 fits into the slit 27b. The slit 27b is a part of the guide-wire securing unit.

The raising wire 30 has one end connected to the riser driving mechanism 41 (see FIG. 7) described later of the operation portion 13, and another end connected to the treatment instrument riser 27. The raising wire 30 is inserted into the insertion portion 12, and an outer circumference of the raising wire 30 is covered with a guide pipe 31. Further, an outer circumference of the guide pipe 31 is covered with a guide tube 32. The treatment instrument riser 27 is configured so as to be raised around the riser rotation support point 28 according to a traction operation of the raising wire 30. Further, a receiving member (hereinafter referred to as insulating member) 77 is arranged at a position opposite to the treatment instrument riser 27 at the distal end of the distal-end hard portion 21.

A depressed guiding surface 77a is formed on a surface of the insulating member 77 at a distal end side and extends in a direction perpendicular to the insertion direction, which is a height direction of FIG. 3. When the treatment instrument riser 27 is raised up to a maximum position, the guide wire 56 is sandwiched between the guiding surface 77a and the slit 27b of the treatment instrument riser 27, whereby the guide wire 56 is secured at the position.

Figure 6:
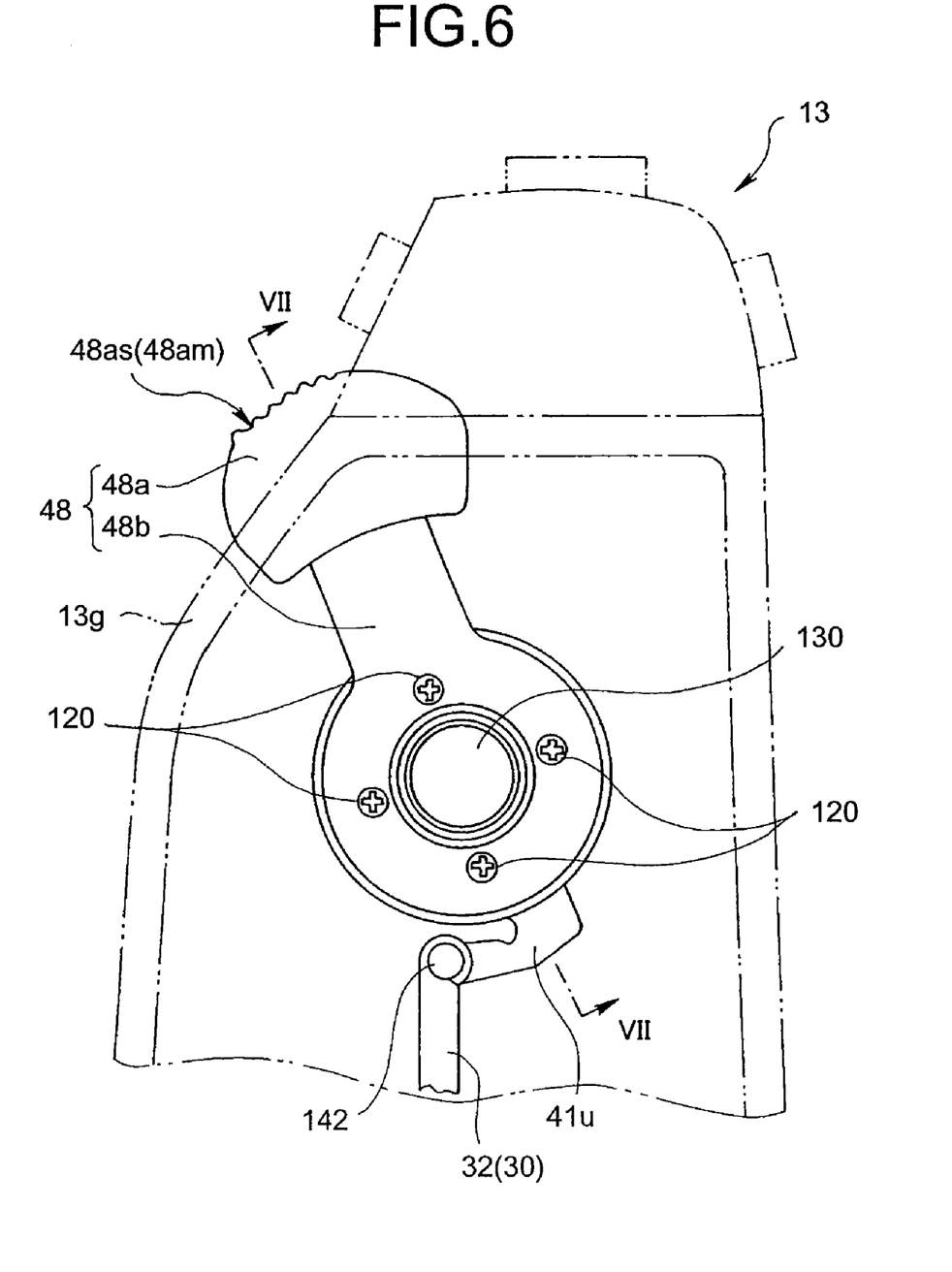
FIG. 6 is a perspective front view of an internal structure of an operation portion of the endoscope of FIG. 1, in particular of a riser driving mechanism to which an operation knob is connected.
Figure 7:
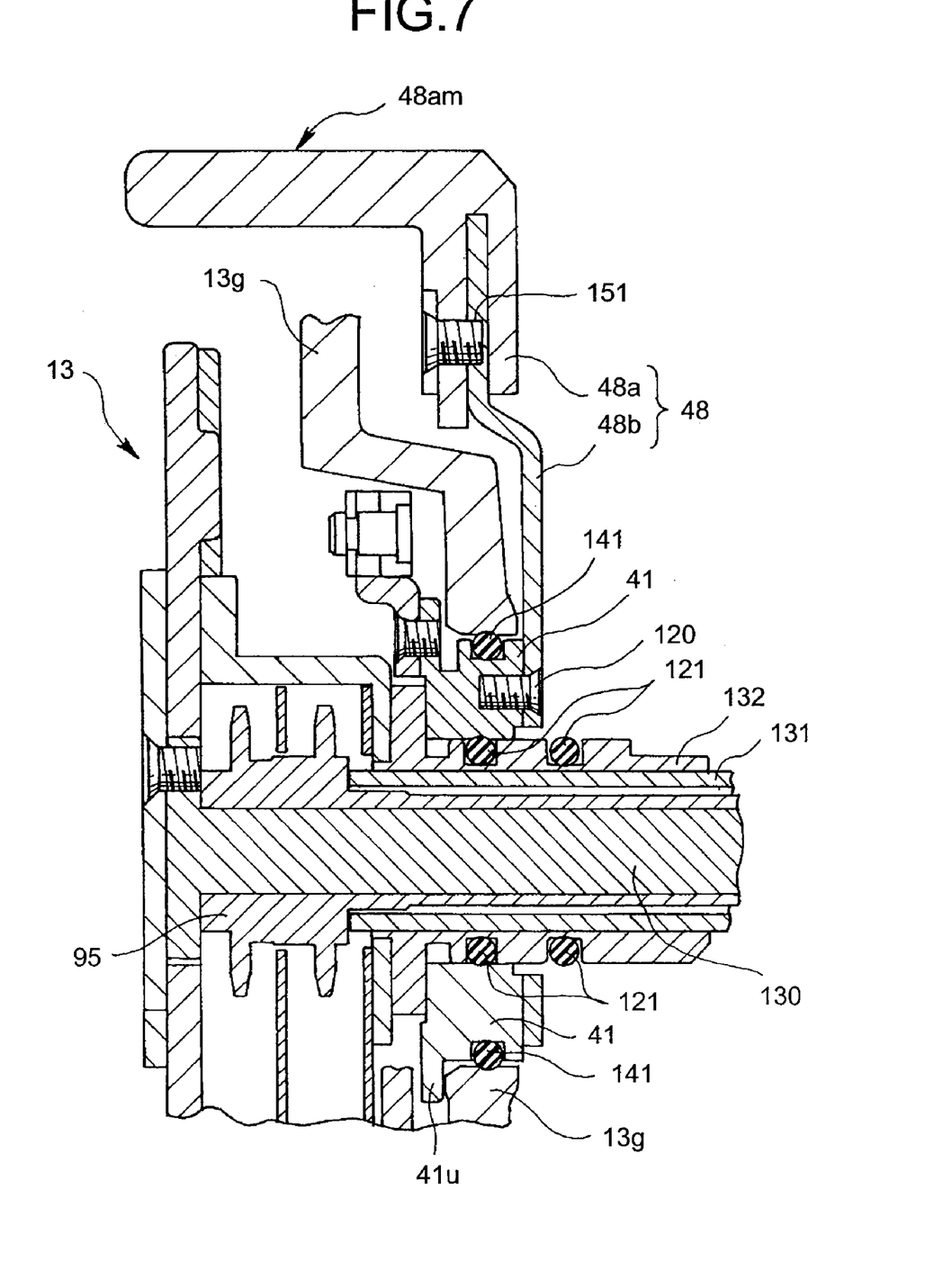
FIG. 7 is a sectional view along line VII-VII of FIG. 6.

FIG. 6 is a schematic front perspective view of an internal structure of the operation portion 13 of the endoscope 1 of FIG. 1, in particular the riser driving mechanism 41 to which the operation knob 48 is connected. FIG. 7 is a sectional view along line VII-VII of FIG. 6.

As shown in FIGS. 6 and 7, a main axis 130 is arranged in the operation portion 13 of the endoscope 1 so that one end of the main axis 130 is fixed inside the operation portion 13 and the main axis 130 protrudes outward from inside the operation portion 13. A bending operation knob 35 (see FIG. 1) fits to and is fixed at another end of the main axis 130 projecting from the operation portion 13, so that the bending operation knob 35 covers an outer circumference and the another end of the main axis 130. Further, a known pulley 95 is rotatably fitted onto an outer circumference of the one end of the main axis 130. A bending operation wire (not shown) is wound around the pulley 95 so that the bendable portion 16 is bent in four directions when the bendable portion 16 in the insertion portion 12 is pulled in four directions according the rotation operation of the bending operation knob 35.

Further, a cylindrical member 131 is secured inside the operation portion 13. The cylindrical member 131 is an axis which is arranged so as to cover the outer circumference of the main axis without being in contact with the main axis 130. Further, an O-ring holding member 132 is arranged around an outer circumference of the cylindrical member 131. The O-ring holding member 132 is an axis which has plural circular grooves, into which O-rings 121 described later fit, on an outer circumference.

A watertight member, which is a securing unit that secures the operation knob 48 at a certain position and represented by an O-ring 121, fits into the groove on the outer circumference of the O-ring holding member 132. The O-ring 121 has such a diameter that the operation knob 48 is kept at the rotated position which is the position the operation knob 48 takes when the treatment instrument riser 27 secures the guide wire 56.

Further, the O-ring 121 has a fastening force with respect to the O-ring holding member 132 so as to maintain the operation knob 48 at the rotated position which is the position the operation knob 48 takes when the treatment instrument riser 27 secures the guide wire 56.

The short-tube-like riser driving mechanism 41 rotatably fits around the outer circumference of the O-ring holding member 132 via the O-ring 121. Hence, the O-ring 121 is placed between the O-ring holding member 132 and the riser driving mechanism 41.

On a side surface of the riser driving mechanism 41, one end of an arm 48b which is a part of the operation knob 48 is secured by a screw 120 or the like.

A grasper 48a, which is a part of the operation knob 48, is secured at another end of the arm 48b by a screw 151, for example. An outer circumference of the grasper 48a is a grasping surface 48am, on which plural protrusions are formed as a slip stopper 48as as shown in FIG. 6.

A grasper 48a, which is a part of the operation knob 48, is secured at another end of the arm 48b by a screw 151, for example. An outer circumferentia of the grasper 48a is a grasping surface 48am, on which plural protrusions are formed as a slip stopper 48as as shown in FIG. 6.

Further, the riser driving mechanism 41 has an arm 41u, on which one end of the raising wire 30 whose another end is secured at the treatment instrument riser 27 is rotatably fixed by a screw 142 or the like.

A circular groove is formed on the outer circumference of the riser driving mechanism 41, and a watertight member, i.e., the securing unit such as the O-ring 141 fits into the groove. The O-ring 141 has such a diameter that the O-ring 141 keeps the operation knob 48 at the rotated position which is the position the operation knob 48 takes when the treatment instrument riser 27 secures the guide wire 56 at the position.

Further, similarly to the O-ring 121, the O-ring 141 has such a fastening force with respect to the riser driving mechanism 41 that the O-ring 141 keeps the operation knob 48 at the rotated position which the operation knob 48 takes when the treatment instrument riser 27 secures the guide wire 56 at the position.

In the embodiment, a wire diameter of the O-ring 141 and a wire diameter of the O-ring 121 are the same. Further, when the O-ring 141 and the O-ring 121 are compared, a position where the O-ring 141 is brought into contact with the riser driving mechanism 41 is located farther from the main axis 130 than a position where the O-ring 121 is brought into contact with the riser driving mechanism 41. Therefore, even when the two O-rings have the same wire diameter, the fastening force applied by the O-ring 141 to the operation knob 48 is larger than the fastening force applied by the O-ring 121 to the operation knob 48. Thus, a sufficient fastening force can be applied to the operation knob 48 without increase in the wire diameter of each of the O-ring 121 and the O-ring 141 as far as possible, whereby the members can be downsized. In the embodiments, the wire diameter of the O-ring 141 and that of the O-ring 121 are the same. However, the O-rings 141 and 121 may have different wire diameters, for example, the wire diameter of the O-ring 141 may be smaller than the wire diameter of the O-ring 121 so that the fastening force exerted by two O-rings to the operation knob 48 are substantially equal.

An outer packaging member 13g of the operation portion 13 is arranged around the outer circumference of the riser driving mechanism 41 via the O-ring 141. Thus, the O-ring 141 is placed between the riser driving mechanism 41 and the outer packaging member 13g of the operation portion 13.

In the description, the fixed state of the operation knob 48 also means a state in which the rotation of the riser driving mechanism 41 is slidably stopped by sliding resistance of the O-ring 121 and the O-ring 141, and the operation knob 48 is kept at the rotated position and does not move unless the operator applies a predetermined force onto the operation knob 48.

An effect of the endoscope 1 according to the embodiment having the above described structure, more specifically, an operation of securing the guide wire 56 with the operation knob 48 will be described.

When the grasper 48a of the operation knob 48 is rotated to one direction, rotational force is transferred to the riser driving mechanism 41 to which the arm 48b of the operation knob 48 is secured, and the riser driving mechanism 41 starts rotating in one direction. Accordingly, the arm 41*u* of the riser driving mechanism 41 starts pulling the raising wire 30.

When the raising wire 30 is pulled, the treatment instrument riser 27, whose lower end is located close to a surface opposite to the channel opening 26 of the distal-end cover 22 rotates in one direction around the riser rotation support point 28, for example, in a clockwise direction in FIG. 3.

In response to the clockwise rotation of the treatment instrument riser 27, the guide wire 56 which runs along the guiding surface 27*a* of the treatment instrument riser 27 is raised toward the channel opening 26. Thereafter, the grasper 48*a* of the operation knob 48 is further rotated in one direction to raise the guide wire 56 running along the guiding surface 27*a* of the treatment instrument riser 27. Then, at a certain rising position, the guide wire 56 fits into the slit 27*b* formed in the guiding surface 27*a* and is further raised.

A subsequent further rotation of the grasper 48*a* of the operation knob 48 in one direction further raises the treatment instrument riser 27 until the treatment instrument riser 27 is brought into contact with a stopper portion not shown. Then, the guide wire 56 fitting into the slit 27*b* comes to be sandwiched between the insulating member 77 and the slit 27*b* of the treatment instrument riser 27, whereby the guide wire 56 is secured at the position.

As described above, the O-ring 121 placed between the O-ring holding member 132 and the riser driving mechanism 41 and the O-ring 141 placed between the riser driving mechanism 41 and the outer packaging member 13*g* of the operation portion 13 have such a diameter that the operation knob 48 is kept at the rotated position which is the position the operation knob 48 takes when the guide wire 56 is secured by the treatment instrument riser 27.

Further, as described above, the fastening force of the O-ring 121 with respect to the O-ring holding member 132 and the fastening force of the O-ring 141 with respect to the riser driving mechanism 41 are such that the treatment instrument riser 27 can keep the operation knob 48 at the rotated position which the operation knob 48 takes when the guide wire 56 is secured.

Therefore, when the guide wire 56 is secured, even when the operator takes off the hand from the grasper 48*a* of the operation knob 48, the riser driving mechanism 41 does not rotate in another direction, i.e., an opposite direction from the above one direction in which the riser driving mechanism 41 is rotated to raise the riser 27, due to sliding resistance of the O-ring 121 and the O-ring 141. In other words, unless the operator applies a force to the operation knob 48, the riser driving mechanism 41 does not rotate in the another direction opposite to the one direction in which the riser driving mechanism 41 is rotated to raise the riser 27 according to the operation of the operation knob 48. In other words, the guide wire 56 would not be released against the will of the operator.

Thereafter, while the guide wire 56 is secured, the operator can withdraw the treatment instrument 55 from the treatment instrument insertion channel 23 using the guide wire 56 as a guide, and insert the next treatment instrument 55 up to the slit 27*b* of the treatment instrument riser 27.

When the guide wire 56 is to be released, the grasper 48*a* of the operation knob 48 is rotated in the opposite direction against the one direction in which the grasper 48*a* is rotated to raise the treatment instrument riser 27 with such a force as to overcome the sliding resistance. Then, the rotational force is transferred to the riser driving mechanism 41 to which the arm 48*b* of the operation knob 48 is fixed, and the riser driving mechanism 41 starts rotating in the another direction. Along with the rotation of the riser driving mechanism 41, the arm 41*u* of the riser driving mechanism 41 starts loosening the raising wire 30.

When the raising wire 30 is loosened, the treatment instrument riser 27 which is in contact with the insulating member 77 starts rotating around the riser rotation support point 28 in another direction, for example, anti-clockwise direction in FIG. 3.

According to the anti-clockwise rotation of the treatment instrument riser 27, the other end of the treatment instrument riser 27 which is in contact with the insulating member 77 is inclined so as to bring the lower end of the treatment instrument riser 27 closer to the lower side of FIG. 3. Thus, the guide wire 56 is released from the position, and it becomes possible to insert/withdraw the guide wire 56 into/from the pancreatic duct, bile duct, hepatic duct, or the like.

In the first embodiment of the present invention, the O-ring 121 placed between the O-ring holding member 132 and the riser driving mechanism 41 and the O-ring 141 placed between the riser driving mechanism 41 and the outer packaging member 13*g* of the operation portion 13 have such a diameter that the operation knob 48 is kept at the rotated position where the operation knob 48 is placed when the treatment instrument riser 27 secures the guide wire 56.

Further, the O-ring 121 fits into the O-ring holding member 132 and the O-ring 141 fits into the riser driving mechanism 41 so that the fastening force of the O-ring 121 with respect to the O-ring holding member 132 and the fastening force of the O-ring 141 with respect to the riser driving mechanism 41 are such that the operation knob 48 is kept at the rotated position which the operation knob 48 takes when the treatment instrument riser 27 secures the guide wire 56 at the position.

Thus, a force exerted by the O-ring 121 to push the O-ring holding member 132 and the riser driving mechanism 41 increases, and at the same time, a force exerted by the O-ring 141 to push the riser driving mechanism 41 and the outer packaging member 13*g* of the operation portion 13 increases. Hence, the sliding resistance between the O-ring 121 and the O-ring holding member 132 and the riser driving mechanism 41 increases while the sliding resistance between the O-ring 141 and the riser driving mechanism 41 and the outer packaging member 13*g* of the operation portion 13 increases.

Therefore, when the guide wire 56 is secured, even if the operator takes off the hand from the grasper 48*a* of the operation knob 48, the riser driving mechanism 41 secured by the operation knob 48 does not rotate in the another direction which is opposite to the one direction. In other words, the rotation of the operation knob 48 is restricted to the one direction. Hence, the guide wire 56 would not be released from the position against the will of the operator.

Hence, even when the operator takes off the hand from the operation knob 48 while the guide wire 56 is secured, the guide wire can be surely kept at the position. Further, since the operator does not need to hold the operation knob 48, the operator can use the hands more freely, whereby the operator can enhance the treatment performance and operability of other treatment instruments.

Further, since merely the change in diameters of the O-rings 121 and 141 or the change in fastening force applied to the members to which the O-rings 121 and 141 fit sufficiently achieves the securing of the guide wire 56, the guide wire 56 can be secured at the position easily at low cost. In the first embodiment, the O-ring which is available at relatively low cost is employed as the watertight member. However, the applicable watertight member is not limited to the O-ring.

Further, since the external shape of the endoscope does not change significantly in comparison with the endoscope to which a securing unit is additionally attached to the outer packaging member 13g of the operation portion 13, efficiency of washing can be maintained as in the conventional apparatus. Further, since an additional securing mechanism for securing the operation knob 48 at the rotated position is not required in the operation portion 13 in the first embodiment, increase in the size of the apparatus can be suppressed. At the same time, various operations with the operation knob 48, such as a raising operation of the guide wire 56, a maintaining operation of the raised state of the guide wire 56, a securing operation of the guide wire 56, and a releasing operation of the guide wire 56, can be easily performed.

Figure 8:
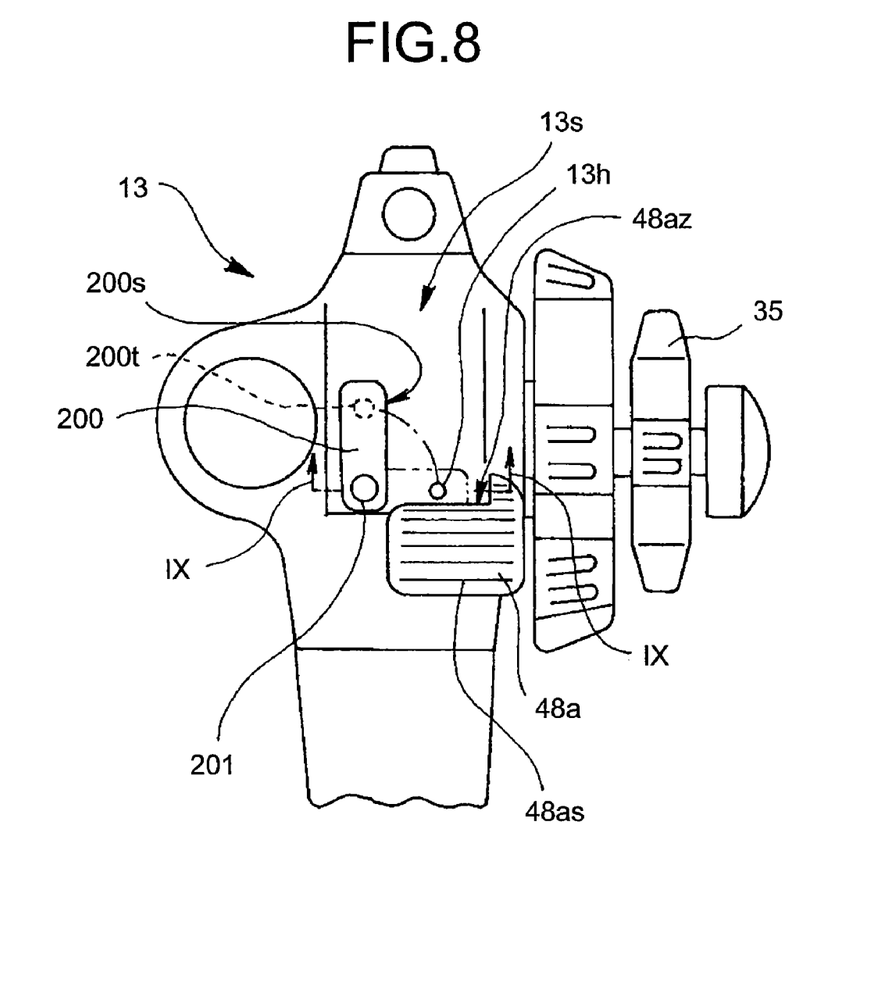
FIG. 8 is a front view of the operation portion, in particular of a modified example of a securing unit which secures the operation knob at a rotated position which is the position the operation knob takes when a guide wire of FIG. 3 is secured.

Modified example of the first embodiment will be described below. FIG. 8 is a front view of the operation portion, in particular, a modified example of the securing unit that secures the operation knob 48 at the rotated position which the operation knob 48 takes when the guide wire 56 of FIG. 2 is secured at the position, and FIG. 9 is a sectional view along line IX-IX of FIG. 8.

In the first embodiment, the rotation of the operation knob 48 is prevented when the guide wire 56 is secured at the position, by varying the diameters of the O-rings 121 and 141, or the fastening force applied to the members to which the O-rings 121 and 141 fit.

The operation knob 48 may be secured when the guide wire 56 is secured with the use of a securing unit provided in the operation portion 13.

Figure 9:
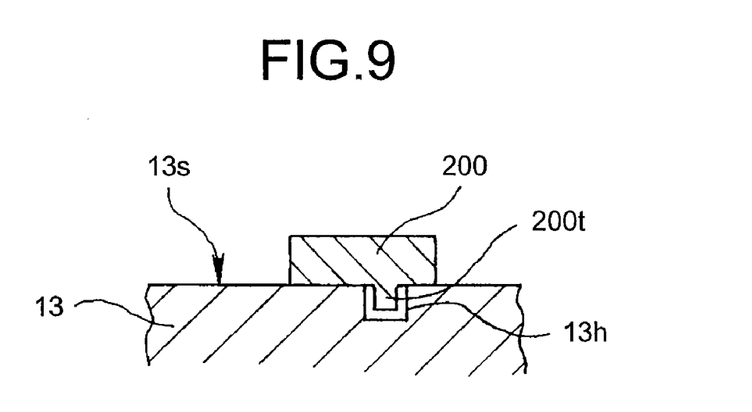
FIG. 9 is a sectional view along line IX-IX of FIG. 8.

Specifically, as shown in FIGS. 8 and 9, a depression 13h is formed at the rotated position of the operation knob 48 on the side surface 13s of the outer packaging member 13g of the operation portion 13 when the guide wire 56 is secured at the position. Further, an operation knob holding member 200 which is a securing unit having a protrusion 200t which is engageable with the depression 13h of the operation portion 13 is rotatably secured at the side surface 13s of the operation portion 13 with a screw 201, for example.

Hence, when the operation knob 48 has not been rotated, in other words, when the treatment instrument riser 27 has not risen to the maximum position to secure the guide wire 56 at the position, the operation knob holding member 200 is positioned so as not to contact with the grasper 48a of the operation knob 48. The protrusion 200t of the operation knob holding member 200 is disengaged from the depression 13h of the operation portion 13.

When the operation knob 48 is rotated and the riser 27 rises to the maximum position to secure the guide wire 56 at the position, the operation knob holding member 200 is rotated in one direction to bring the side surface 200s of the operation knob holding member 200 into contact with a side surface 48az of the grasper 48a of the operation knob 48. Then, the protrusion 200t of the operation knob holding member 200 is fitted into the depression 13h of the operation portion 13 as shown in FIG. 9. Thus, the rotation of the operation knob 48 is stopped.

Thereafter, when it is desirable to release the guide wire 56 from the position, the operation knob holding member 200 is rotated in an opposite direction to the one direction, whereby the side surface 200s of the operation knob holding member 200 is separated from the side surface 48az of the grasper 48a of the operation knob 48 and the protrusion 200t of the operation knob holding member 200 is disengaged from the depression 13h of the operation portion 13. Then, the operation knob 48 is rotated in an opposite direction to the one direction, whereby the guide wire 56 is released from the position.

Thus, the operation knob 48 can be secured easily and surely at the rotated position which is the position the operation knob 48 takes when the guide wire 56 is secured with the use of the operation knob holding member 200 provided in the operation portion 13. Further, since the rotation of the operation knob 48 can be stopped without the need of a securing unit for stopping the rotation of the operation knob 48 in the riser driving mechanism 41 and the raising wire 30, the treatment instrument riser 27 can be raised without the need of change in the force applied to rotate the operation knob 48.

Other effects of the modified example are the same as those of the first embodiment. When the force applied to rotate the operation knob 48 is ignorable, better securing effect can be obtained by restricting the rotation of the operation knob 48 when the guide wire 56 is secured, by using the O-rings 121 and 141 in addition to the operation knob holding member 200.

Figure 10:
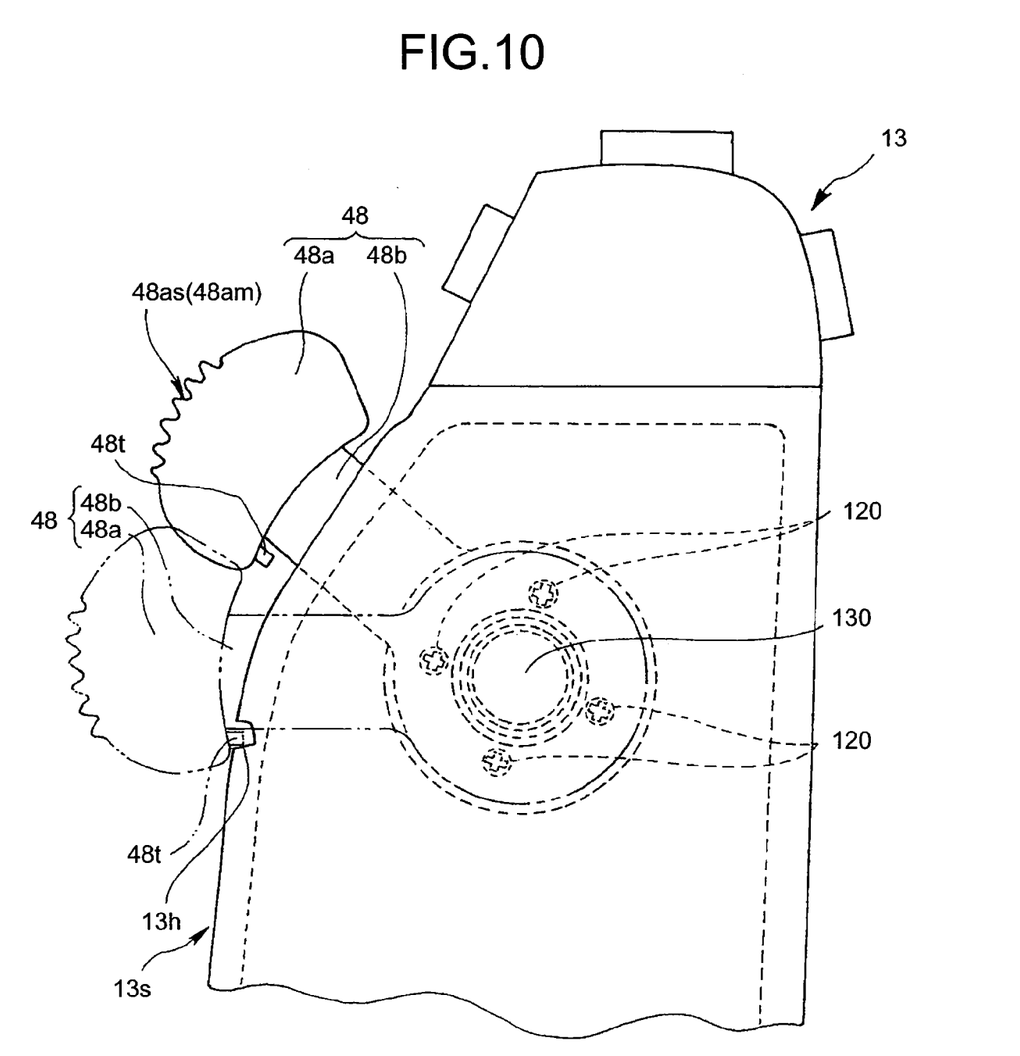
FIG. 10 is a front view of the operation portion, in particular of another modified example of the securing unit which secures the operation knob at the rotated position which the operation knob takes when the guide wire of FIG. 3 is secured.

Another modified example will be described below. FIG. 10 is a front view of the operation portion, in particular, of another modified example of a securing unit for securing the operation knob 48 at the rotated position which the operation knob 48 takes when the guide wire 56 of FIG. 3 is secured.

The operation knob 48 may be secured when the guide wire 56 is secured at the position with the use of a protrusion provided in the grasper 48a of the operation knob 48.

Specifically, as shown in FIG. 10, a depression 13h is formed at a position on the side surface 13s of the outer packaging member 13g of the operation portion 13. When the operation knob 48 is rotated until the guide wire 56 is secured, the operation knob 48 comes to the position where the depression 13h is formed. Further, a protrusion 48t which is a securing unit is formed in the grasper 48a of the operation knob 48 on a surface opposing to the side surface 13s of the operation portion 13.

When the operation knob 48 is not rotated, in other words, when the riser 27 does not rise to the maximum position to secure the guide wire 56 at the position, the protrusion 48t of the grasper 48a of the operation knob 48 is disengaged from the depression 13h of the operation portion 13.

When the operation knob 48 is rotated and the riser 27 rises to secure the guide wire 56 at the position, the protrusion 48t of the grasper 48a of the operation knob 48 is fitted into the depression 13h of the operation portion 13 as shown in FIG. 10. Thus, the rotation of the operation knob 48 is stopped.

Thereafter, when it is desirable to release the guide wire 56, the operation knob 48 is rotated in another direction, which is opposite to the one direction, and the protrusion 48t of the grasper 48a of the operation knob 48 is disengaged from the depression 13h of the operation portion 13. Thus, the guide wire 56 is released.

As described above, since the operation knob 48 is secured when the guide wire 56 is secured with the use of the protrusion 48t provided in the grasper 48a of the operation knob 48, the securing can be achieved easily and securely with a simplified structure. Further, since the rotation of the operation knob 48 can be stopped without the need of a securing unit for stopping the rotation of the operation knob 48 in the riser driving mechanism 41 and the raising wire 30, the treatment instrument riser 27 can be raised without the need of change in force applied to rotate the operation knob 48.

Other effects of the modified example are the same as those of the first embodiment. If the force applied to rotate the operation knob 48 is ignorable, better securing effect can be obtained by restricting the rotation of the operation knob 48 when the guide wire 56 is secured by using the operation knob holding member 200 and the O-rings 121 and 141, in addition to the protrusion in the operation knob 48.

Figure 11:
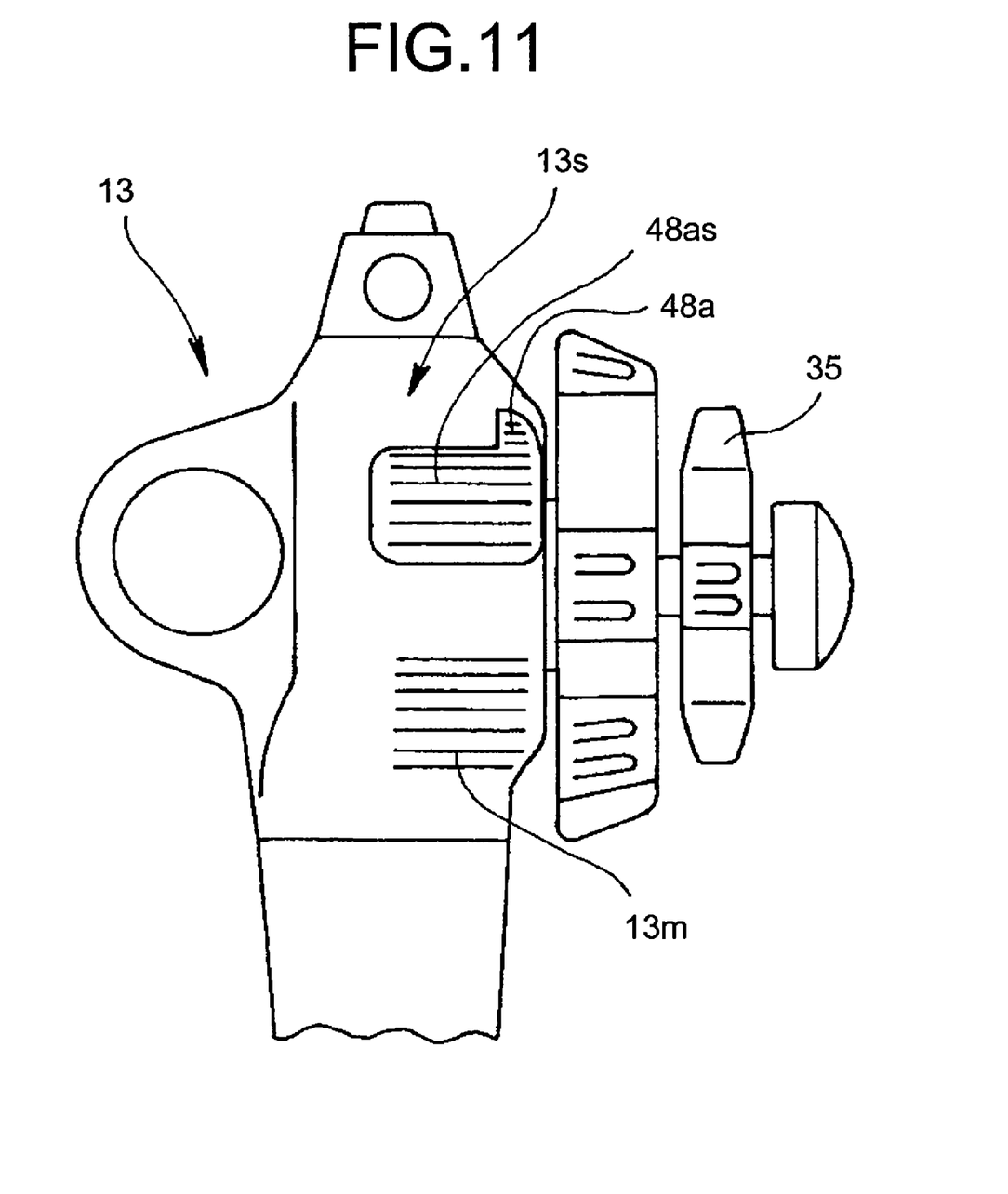
FIG. 11 is a front view of the operation portion, in particular of still another modified example of the securing unit which secures the operation knob at the rotated position which the operation knob takes when the guide wire of FIG. 3 is secured.

Further, a still another modified example will be described. FIG. 11 is a front view of the operation portion, in particular, of a still another modified example of the securing unit for securing the operation knob 48 at the rotated position which is the position the operation knob 48 takes when the guide wire 56 of FIG. 3 is secured.

The operation knob 48 may be secured when the guide wire 56 is secured with the use of a friction generating member provided in the operation portion 13.

Specifically, as shown in FIG. 11, a friction generating member 13m which is a securing unit consisting of plural depressions and protrusions is formed on the side surface 13s of the outer packaging member 13g of the operation portion 13. When the operation knob 48 is rotated until the guide wire 56 is secured, the operation knob 48 comes to the position where the friction generating member 13m is formed.

When the operation knob 48 is not rotated, in other words, when the riser 27 has not risen to the maximum position to secure the guide wire 56, the grasper 48a of the operation knob 48 is separated from the friction generating member 13m of the operation portion 13.

When the operation knob 48 is rotated and the riser 27 rises to the maximum position to secure the guide wire 56, the grasper 48a of the operation knob 48 is held by friction force between the grasper 48a and the friction generating member 13m of the operation portion 13.

Thereafter, when it is desirable to release the guide wire 56, the operation knob 48 is rotated in another direction which is an opposite direction to the one direction, and the grasper 48a of the operation knob 48 is separated from the friction generating member 13m of the operation portion 13. Thus, the guide wire 56 is released.

Since the operation knob 48 is secured when the guide wire 56 is secured with the use of the friction force generated by the friction generating member 13m provided on the side surface 13s of the operation portion 13, the securing can be achieved easily and securely with a simplified structure.

Further, since the rotation of the operation knob 48 can be stopped without the need of a securing unit for stopping the rotation of the operation knob 48 in the operation knob 48, the riser driving mechanism 41, and the raising wire 30, the treatment instrument riser 27 can be raised without the need of change in the force applied to rotate the operation knob 48.

Further, a position where the friction generating member 13m is provided is not limited to the position according to the embodiment, and the friction generating member 13m can be provided at any position as far as the friction generating member 13m can secure the operation knob 48 at the rotated position when the guide wire 56 is secured at the position.

Other effects of the modified example are the same as those of the first embodiment. If the force applied to rotate the operation knob 48 is ignorable, better securing effect can be obtained by restricting the rotation of the operation knob 48 when the guide wire 56 is secured by using the protrusion 48t of the operation knob 48, the operation knob holding member 200, and the O-rings 121 and 141, in addition to the friction generating member 13m.

Figure 12:
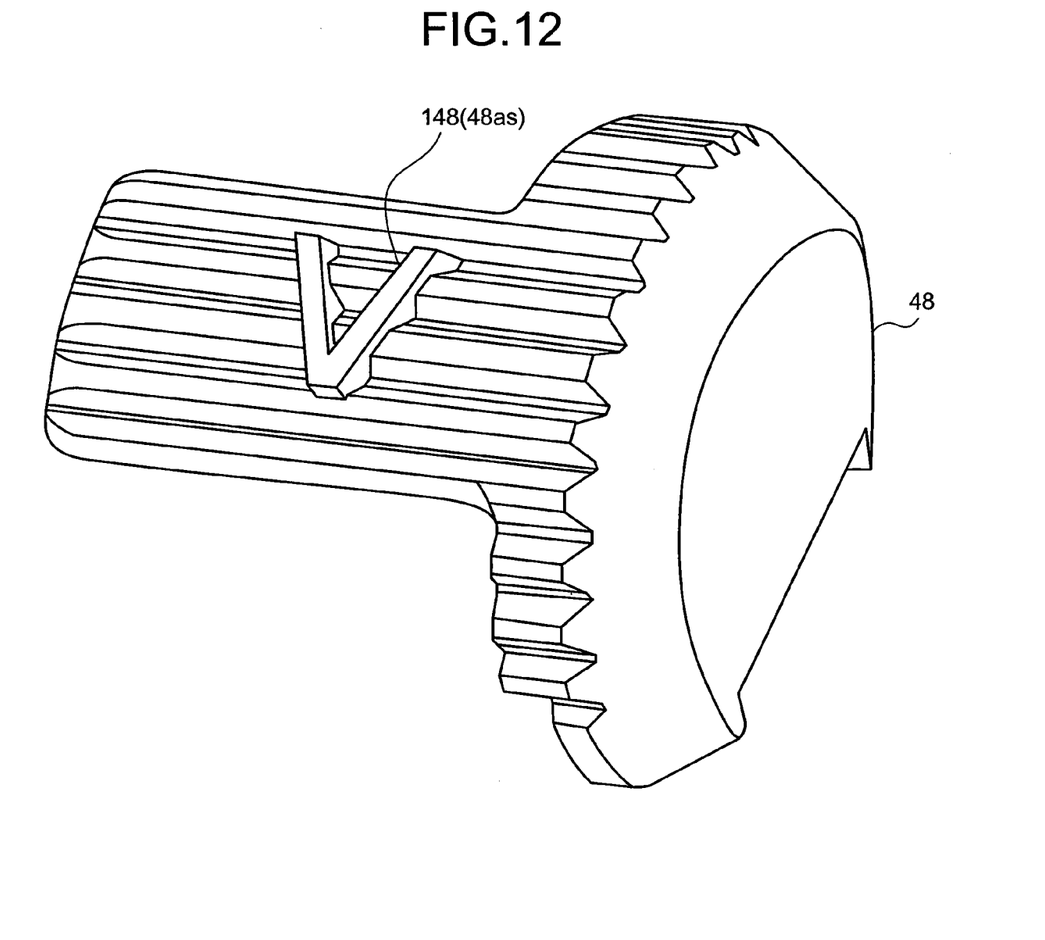
FIG. 12 is an enlarged perspective view of a grasper, in particular of a modified example of a slip stopper formed on a grasping surface of the grasper in the operation portion of FIG. 1.

A still further modified example will be described below. FIG. 12 is an enlarged perspective view of the grasper, in particular, a still further modified example of a slip stopper formed on the grasping surface of the grasper in the operation knob of FIG. 1.

In the first embodiment, the outer circumference of the grasper 48a is the grasping surface 48am which is held by the operator during the operation. The slip stopper 48as on the grasping surface 48am is shown to be formed with plural protrusions.

The form of the slip stopper 48 as is, however, not limited to the above. As shown in FIG. 12, the slip stopper 48 as may be formed with an embossed character in addition to the plural protrusions. For example, the slip stopper 48 as may be a character 148 of a "V" shape, for example, indicating an endoscope with a guide wire securing function. When the character 148 of the "V" shape indicating the endoscope with the guide wire securing function is formed on the grasping surface 48am, the operator can readily recognize that the endoscope under the use has the guide wire securing function by touching the same with a finger without having a look at the endoscope.

The character 148 formed on the grasping surface 48am is not limited to "V". The character 148 may be "GW" indicating the guide wire, for example. The character 148 may be any character as far as the character 148 allows the operator to recognize that the endoscope under use has the guide wire securing function. Further, the character 148 may indicate the size of the guide wire which can be held in the slit 27b of the treatment instrument riser 27. For example the character 148 may be "0.035" or "0.025".

Further, when the character 148 is formed on the grasping surface 48am of the grasper 48a, the operator can recognize that the endoscope has the guide wire securing function while performing the operation for securing the guide wire 56 at the position. Therefore, the operator is prevented from taking a conventional endoscope as the endoscope having the guide wire securing function and from mistakenly thinking that he/she has secured the guide wire 56 by rotating a different operation knob.

Further, the character is not limited to a character indicating the endoscope having the guide wire securing function. Any character which allows for distinction between the endoscope with the guide wire securing function and the endoscope without the same is usable.

To make the operator easily recognize that the endoscope has the guide wire securing function, it is effective to configure the grasper 48a of the operation knob 48 in a different color from the color of the bending operation knob 35 as shown in FIG. 12, in addition to form the embossed character 148 on the grasping surface 48am of the grasper 48a of the operation knob 48.

For example, the bending operation knobs 35 are mostly black in general. Then, if the operation knob 48 is formed to have fluorescent color, for example, the operator can easily recognize that the endoscope has the guide wire securing function even in a dark examination room. The color of the grasper 48a is not limited to the color indicating the endoscope with the guide wire securing function, and may indicate the endoscope without the guide wire securing function.

Figure 13:
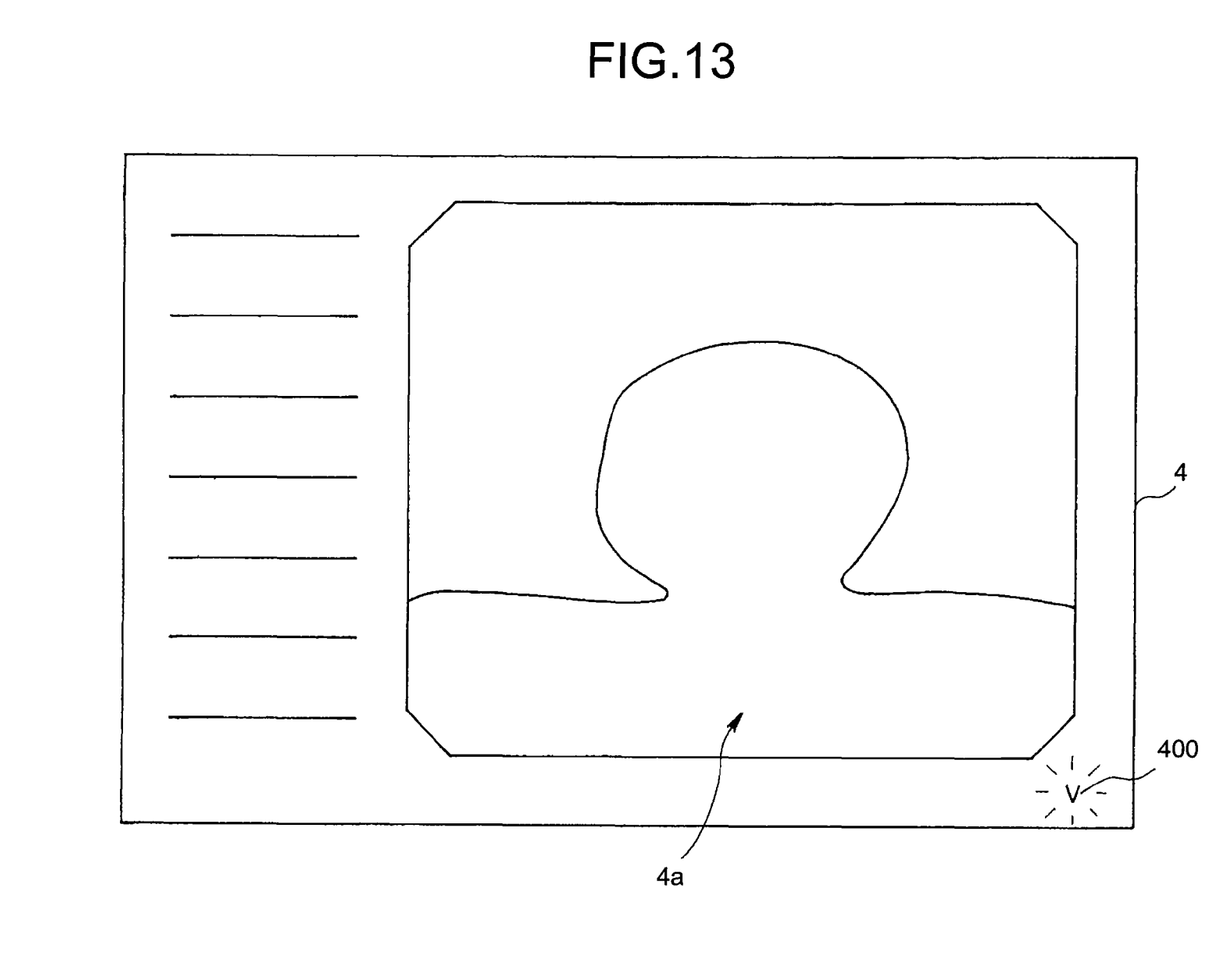
FIG. 13 shows a modified example of a monitor of FIG. 1 according to which an operator is made to recognize that an endoscope in use has a guide wire securing function.

Further, in order to make the operator recognize that the endoscope has the guide wire securing function, a character 400 of "V" indicating the endoscope with the guide wire securing function may be displayed in a lower portion of a monitor screen 4a of the monitor 4, for example, as shown in FIG. 13, and the character 400 may be lighted so that the operator can visually recognize the same. The manner of display of the character 400 of "V" is not limited to lighting and may be blinking.

FIG. 13 shows a modified example of making the operator recognize that the endoscope has the guide wire securing function using the monitor 4 of FIG. 1.

Here, any character can be displayed on the monitor 4 as far as the character allows the operator to recognize that the endoscope has the guide wire securing function. Further, the position where the character 400 is lighted is not limited to the lower portion of the monitor 4 and can be on the monitor screen 4*a*. The character 400 can be shown at any position as far as the position is on the monitor 4. Further, the character 400 may not indicate the endoscope with the guide wire securing function and may indicate other types of endoscope.

In the embodiments as described above, the treatment instrument riser 27 is shown to have a function of a guide-wire securing unit. The guide-wire securing unit and the treatment instrument riser 27 may be provided separately, however. Then, the guide wire securing operation member that works on the guide wire securing unit to secure the guide wire may be arranged at a fixed position separately from the operation knob 48.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
a treatment instrument riser configured to guide a distal end of a treatment instrument projecting from a distal end opening provided in a channel for inserting the treatment instrument in an insertion portion to a desired position;
a driving mechanism which is rotatably fitted onto an axis provided in an operation portion covered with an outer packaging member, and is configured to drive the treatment instrument riser;
a guide-wire securing unit provided on the treatment instrument riser and configured to secure a position of a guide wire projecting from the distal end opening provided in the channel in the insertion portion;
a guide-wire securing operation member connected to the driving mechanism and configured to operate the guide-wire securing unit, the guide-wire securing operation member including an operation knob configured to secure a position of the guide wire by operating the driving mechanism of the treatment instrument riser with a rotation via the driving mechanism; and
a securing unit configured to secure a position of the guide-wire securing operation member in a state where the position of the guide-wire is secured, wherein
the securing unit comprises a first O-ring which is positioned between the axis and the driving mechanism and fits into a first groove formed on an O-ring holding member arranged around an outer surface of the axis, and a second O-ring which is positioned between the driving mechanism and the outer packaging member and fits into a second groove formed on an outer surface of the driving mechanism, wherein
the first and second O-rings are comprised of watertight members and are configured to cause the rotated position of the operation knob to be maintained when a position of the guide wire is secured by the guide-wire securing unit, wherein
a wire diameter of the first O-ring and a wire diameter of the second O-ring are the same so that the rotated position of the operation knob is maintained when a position of the guide wire is secured by the guide-wire securing unit, and
a fastening force applied by the second O-ring to the operation knob is larger than a fastening force applied by the first O-ring to the operation knob so that the rotated position of the operation knob is maintained when a position of the guide wire is secured by the guide-wire securing unit.

* * * * *